United States Patent [19]

Kim

[11] Patent Number: 4,814,335

[45] Date of Patent: * Mar. 21, 1989

[54] ANTIVIRAL COMPOUNDS

[75] Inventor: Sun H. Kim, Chestnut Hill, Mass.

[73] Assignee: Biomeasure, Incorporated, Hopkinton, Mass.

[*] Notice: The portion of the term of this patent subsequent to Nov. 25, 2003 has been disclaimed.

[21] Appl. No.: 66,262

[22] Filed: Jun. 23, 1987

Related U.S. Application Data

[63] Continuation-in-part of Ser. No. 923,955, Oct. 28, 1986, abandoned, which is a continuation-in-part of Ser. No. 895,886, Aug. 12, 1986, abandoned, which is a continuation of Ser. No. 541,777, Dec. 31, 1983, Pat. No. 4,625,026, which is a continuation-in-part of Ser. No. 454,732, Dec. 30, 1982, abandoned.

[51] Int. Cl.$^4$ .................. A61K 31/505; C07D 487/00
[52] U.S. Cl. ..................... 514/257; 514/260; 544/249; 544/253
[58] Field of Search ............... 544/249, 253; 514/257, 514/260

[56] References Cited

U.S. PATENT DOCUMENTS

| | | |
|---|---|---|
| 3,057,467 | 10/1962 | Williams . |
| 3,168,521 | 2/1965 | Wagner .................... 544/253 |
| 3,185,691 | 5/1965 | Pribyl . |
| 3,257,400 | 6/1966 | Wagner . |
| 3,398,826 | 8/1968 | Clancy . |
| 3,609,152 | 9/1971 | Hess . |
| 3,786,615 | 1/1974 | Bauer . |
| 3,915,976 | 10/1975 | Salmond .................... 544/253 |
| 3,941,787 | 3/1976 | Salmond . |
| 4,093,715 | 6/1978 | Lin . |
| 4,093,716 | 6/1978 | Lin . |
| 4,279,819 | 7/1981 | Price . |
| 4,355,032 | 10/1982 | Verheyden . |

FOREIGN PATENT DOCUMENTS 7424271 10/1972 Japan .

OTHER PUBLICATIONS

Chem. Abstract, 55:17664h, (1961).
Field et al., (1983), Proc. Nat'l Acad. Sci., U.S.A., 80:4139-43.
Senga et al., (1982), J. Med. Chem., 21:213-49.
Hadden, TIPS, (May, 1982).
Ashton et al., (1982), BBR3, 108:1716-21.
Gupta et al., Indian J. of Chem., "A Novel Class of Hypoglycaemic Agents: Syntheses & SAR in 2-Substituted 4(3H)-Quinazolones, 2-Substituted 4-Hydroxy Polymethylene[5,6]pyrimidines & 3-Substituted 4-Oxo-pyrido[1,2-a]pyrimidines", 9:201-206, (1971).
Ashton et al., CA 79-142777p, (1973).
Vodopyanov, CA 77-61940t, (1972).
Rosowsky et al., CA 78-72051a, 72049f.
Priest et al., CA 82-12907g.

Primary Examiner—Donald G. Daus
Assistant Examiner—Cecilia Shen

[57] ABSTRACT

In one aspect, compounds having antiviral activity and having the general formula:

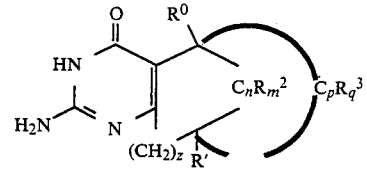

wherein each $R^2$, independently, is H or lower (fewer than 6 carbon atoms) alkyl; each $R^3$, independently, is H or lower alkyl; $R^0$ is H or lower alkyl; $R^1$ is H or lower alkyl; $1 \leq n \leq 11$; $n-2 \leq m \leq 2n$; $0 \leq p \leq 3$; z is 0 or 1; and $p \leq 1 \leq 2p$; each n, m, p, and q being selected so that the sp$^3$ valence shell of each carbon atom in each ring is filled; or a pharmaceutically acceptable salt thereof.

10 Claims, 1 Drawing Sheet

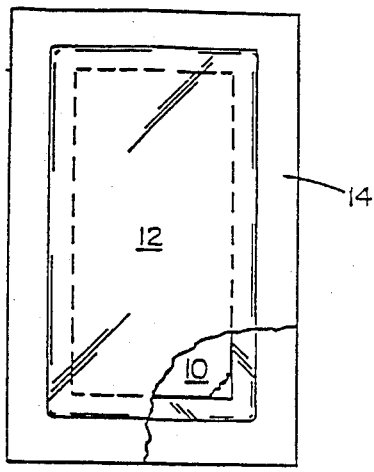

ANTIVIRAL COMPOUNDS

BACKGROUND OF THE INVENTION

This application is a continuation in part of Kim U.S. patent application Ser. No. 923,955, filed Oct. 28, 1986, now abandoned which in turn is a continuation-in-part of Kim U.S. patent application Ser. No. 895,886, filed Aug. 12, 1986, now abandoned which in turn is a continuation of Kim U.S. patent application Ser. No. 541,777, filed Dec. 31, 1983, now U.S. Pat. No. 4,625,026, issued Nov. 25, 1986, which in turn is a continuation-in-part of Kim U.S. patent application Ser. No. 454,732, filed Dec. 30, 1982, which is now abandoned.

This invention relates to biological response modifiers.

SUMMARY OF THE INVENTION

In general, the invention features, in one aspect, compounds having in vivo biological response-modifying activity and having the general formula:

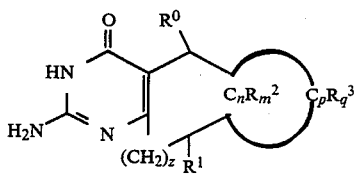

wherein each $R^2$, independently, is H or lower (fewer than 6 carbon atoms) alkyl; each $R^3$, independently, is H or lower alkyl; $R^0$ is H or lower alkyl; $R^1$ is H or lower alkyl; $1 \leq n \leq 11$; $n-2 \leq m \leq 2n$; $0 \leq p \leq 3$; z is 0 or 1; and $p \leq 1 \leq 2p$; each n, m, p, and q being selected so that the $sp^3$ valence shell of each carbon atom in each ring is filled; or a pharmaceutically acceptable salt thereof.

In preferred embodiments, the antiviral compound is 2-amino-4-oxo-5,6,7,8-tetrahydroquinazoline; 2-amino-5,6,7,8,9-pentahydrocyclohepta (d) pyrimidin-4-ol; or 2-amino-5,6,7,8,9,10,11,12,13,14-decahydro-cyclododeca (d) pyrimidin-4-ol.

In another aspect, the invention features compounds having biological response-modifying activity and having the general formula:

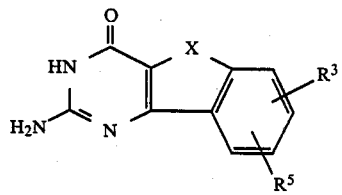

wherein X is $(CH_2)n$ where $1 \leq n \leq 3$;

where $R^4$ is lower alkyl; $CH_2S$; or $CH_2O$; $R^3$ and $R^5$, independently, are H, fluoro, nitro, amino, lower alkylamino, lower dialkylamino, lower arylamino, acylamido (more preferably lower acylamido, e.g., trifluoroacetylamido), carboxy, azido, lower alkoxy, trimethylsulfonyl, trifluoromethanesulfonyl, or lower alkoxycarbonyl (containing an ester linkage), provided that, when X is $(CH_2)_2$, $R^3$ cannot be H; or a pharmaceutically acceptable salt thereof.

In a preferred embodiment the compound is 2-amino-10-fluoro-4-oxo-5,6,7-trihydrobenzocyclohepta (6,5-d)-pyrimidine; 2-amino-10-nitro-4-oxo-5,6,7-trihydrobenzo-cyclohepta (6,5-d)-pyrimidine; 2-amino-10-azido-4-oxo-5,6,7-trihydrobenzocyclohepta (6,5-d)-pyrimidine; or 2,10-diamino-4-oxo-5,6,7-trihydrobenzocyclohepta (6,5-d)-pyrimidine.

In another aspect the invention features compounds having biological response-modifying activity and having the general formula:

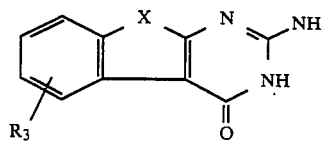

wherein X and $R_3$ are as defined above for Formula (2), of a pharmaceutically acceptable salt thereof.

The compounds exhibit potent biological response-modifying activity. In other words, they exhibit antiviral, antibacterial, and anticancer activity. They are also chemically stable, are not toxic to mammals, and do not decompose in the stomach. The compounds can be particularly valuable in the treatment of immunocomprised patients, e.g., cancer patients, who are at risk of contracting viral infections, particularly herpes simplex virus type II infections. They are also useful in treating cancer, particularly melanoma, alone or in combination with other anti-cancer agents.

Other features and advantages of the invention will be apparent from the following description of the preferred embodiments, and from the claims.

DESCRIPTION OF THE PREFERRED EMBODIMENTS

We turn now to a description of preferred embodiments of the invention.

DRAWING

The FIGURE is a plan view, partially broken away, of a packet containing a towlette impregnated with a biological response-modifying compound of the invention.

STRUCTURE

The compounds have the general formulae recited in the Summary of the Invention above. Examples of preferred compounds within those formulae are those referred to as preferred embodiments above.

The compounds all contain an aminopyrimidone ring fused to a non-aromatic ring. A third ring can also be present.

For Formula (1) compounds, where there is no third ring present, the non-aromatic ring can contain up to 15 carbon atoms. When there is a third ring present, the second ring will generally contain fewer carbon atoms, i.e., 6 or less; i.e., n will be 1 or 2 when p is greater than 0.

The compounds, or pharmaceutically acceptable salts thereof, can be administered alone or in combination with a pharmaceutically acceptable carrier.

Acceptable salts include those made with, e.g., hydrochloric, hydrobromic, hydroiodic, sulfuric, maleic, or fumaric acid; or with potassium, sodium hydroxide, or dicyclohexylamine.

For oral administration the pharmaceutical composition can most conveniently be in the form of capsules or tablets. The composition can also take the form of an ingestible liquid, e.g., syrup. The compounds can also be provided in the form of topical preparations, e.g., ointments, lotions, creams, powders, and sprays.

Referring now to the FIGURE, flexible sheet 10 of fibrous, absorbant paper can be impregnated with a biological response-modifying compound of the invention, diluted, if desired, with a carrier, e.g., distilled water. The impregnated towelette 10 is folded and enclosed in rectangular, sealed, gas tight envelope 12, having fused periphery 14, in a manner such as is described in Clancy U.S. Pat. No. 3,398,826 or Williams U.S. Pat. No. 3,057,467, hereby incorporated by reference. The towelette is impregnated using conventional techniques, e.g., that disclosed in Bauer U.S. Pat. No. 3,786,615, hereby incorporated by reference.

Synthesis

To synthesize a compound of Formula 1, 2, or 3, a mixture of the appropriate alpha-ketoester and guanidine carbonate in xylene is refluxed overnight, and the final product is then collected by filtration and purified.

The alpha-ketoester, if not commercially available, can be prepared by any of several methods, e.g., the reaction of a cyclic ketone with diethyloxalate followed by pyrolysis; or esterification of the commercially available alpho-keto acid, e.g., camphor carboxylic acid; or the reaction of a cyclic ketone with diethylcarbonate at elevated temperature in the presence of guanidine salts in an appropriate solvent, e.g., alcohols, xylene, toluene.

General references describing the synthesis of alpha-ketoesters can be found in *The Pyrimidines*, A. Weissberger, Ed., Interscience, New York, 1962; J. Org. Chem., 30, 1837 (1965); J. Org. Chem 33, 4288 (1968); J. Het. Chem. 7, 197 (1970); J. Het. Chem., 13, 675 (1976); Org. Syn. 47, 20 (1967).

Another method of synthesizing a compound of Formula 1, 2, or 3 involves the formation of a 2,4-diaminopyrimidine derivative by the reaction of a cyclic ketone with dicyandiamide, either in the absence of or in an appropriate solvent, e.g., dimethylformamide, ethoxyethoxyethanol, followed by selective hydrolysis of one amino group.

Specific compounds of Formula (1) were made as follows.

2-amino-4-oxo-5,6,7,8-tetrahydroquinazoline

A mixture of ethyl-2-cyclohexanone carboxylate (2.0 g) and guanidine carbonate (2.66 g) in xylene (40 ml) was refluxed overnight; after cooling the solid was collected by filtration, washed with water, methanol, and dried over $MgSO_4$. 0.6 g of a white solid having a m.p. >300° C. was recovered. The solid was dissolved in Con. HCl, and excess HCl was removed in vacuo to dryness. The gummy residue was treated with methanol-ether to afford a colorless plate (0.6 g).

2-amino-5,6,7,8,9-pentahydro cyclohepta (d) pyrimidin-4-ol

A mixture of ethyl-2-cycloheptanone carboxylate (880 mg) and guanidine carbonate (950 mg) in xylene (20 ml) was refluxed overnight; after cooling, the white solid was collected by filtration, washed with water, and dried. The crude product was recrystallized from methanol. Mass: 179 (mol. ion).

2-amino-5,6,7,8,9,10,11,12,13,14-decahydrocyclododeca (d) pyrimidin-4-ol

A mixture of ethyl-2-cyclododecanone carboxylate (4.0 g) and guanidine carbonate (3.12 g) in xylene (50 ml) was refluxed overnight; after cooling the white solid was collected by filtration, washed with water, and recrystallized from ethanol. 2.15 g of white powder were recovered.

2-amino-5,6,7,8,9,10-hexahydrocycloocta (d) pyrimidin-4-ol

A mixture of ethyl-2-cyclooctanone carboxylate (3.5 g) and guanidine carbonate (3.82 g) in xylene (50 ml) was refluxed overnight; after cooling the white solid was collected by filtration, washed with water, and dried to yield 2.0 g of product.

Specific compounds of Formula (2) were made as follows.

2-amino-10-fluoro-4-oxo-5,6,7-trihydrobenzocyclohepta (6,5-d) pyrimidine

First, 3-nitrobenzosuberone was prepared as follows.

To a stirred mixture of fuming nitric acid (36 ml, density 1.49 g/ml) and concentrated sulfuric acid (18 ml) cooled to $-15°$ C. was added slowly benzosuberone (15 g). The temperature was maintained below $-10°$ C. during addition. When the addition was complete, the mixture was stirred for another hour. It was then poured into a large excess of ice, and the resulting pale yellow solid was collected by filtration, washed with ice water, and dissolved in ethylacetate (700 ml). The ethylacetate solution was washed with 5% aqueous $NaHCO_3$ followed by water, and then dried over anhydrous $MgSO_4$. After evaporation of solvent, the residue was recrystallized from ethanol to give 12.33 g of 3-nitrobenzosuberone. TLC (Silica gel: $CHCl_3$) Rf=0.35.

Second, 3-nitrobenzosuberone was converted to 3-nitrobenzosuberone ethyleneketal as follows. A mixture of 3-nitrobenzosuberone (12.1 g) and ethyleneglycol (16.6 ml) in benzene (210 ml) containing p-toluenesulfonic acid (0.4 g) was refluxed using a Dean-Stark Trap for 6 hours. The benzene layer was separated, washed with 5% aqueous $NaHCO_3$ and water, and then dried over $MgSO_4$. The solvent was evaporated in vacuo to give 11.2 g of 3-nitrobenzosuberone ethyleneketal as a pale yellow solid. TLC (Silica gel: $CHCl_3$) Rf=0.38.

Third, 3-nitrobenzosuberone ethyleneketal was converted into 3-aminobenzosuberone ethyleneketal as follows. To a solution of 3-nitrobenzosuberone ethyleneketal (14.17 g) in ethanol-tetrahydrofuran (4:1, 100 ml) was added 0.4 g 10% palladium-charcoal; hydrogenation was carried out at room temperature under 30 psi atmosphere overnight. The reaction mixture was filtered through celite pad, washed with ethylacetate, and the filtrate concentrated in vacuo to give 12.15 g of the product. TLC (Silica gel: $CHCl_3$/Acetone=9:1) Rf=0.31.

Fourth, 3-aminobenzosuberone ethyleneketal was converted into 3-aminobenzosuberone as follows. 3-aminobenzosuberone ethyleneketal (12.15 g) was dissolved in 2N HCl (150 ml) and stirred at room temperature for 2 hours. The solution then was basified to pH 11–12 using 10N-NaOH and extracted with dichloromethane. The organic extracts were combined and dried ($MgSO_4$), and the solvent removed in vacuo to give 9.4 g of product. TLC (Silica gel: $CHCl_3$/Methanol=9:1) Rf=0.58.

Fifth, 3-aminobenzosuberone was converted into 3-fluorobenzosuberone via a standard Schieman reaction as follows. (General references describing the Schieman reaction are listed in J. March, Advanced Organic Chem. 647 (1986)). To an ice-cooled solution of 3-aminobenzosuberone (12.43 g) in 2N HCl (50 ml) was added gradually a cold solution of NaNO₂ (5.85 g) in water (16 ml). When addition was complete, 65% hexafluorophosphoric acid (14.9 ml) was added, and the reaction was stirred at 0° C. for 30 minutes. The brownish white solid formed was collected by filtration, washed with cold water, washed with small amounts of ether-methanol (9:1), and dried. It was then added in portions to hot xylene (bath temp. 125°–130° C.) and, after gas evolution ceased, the mixture was fractionally distilled to give 101 g of the product as a colorless liquid at 84°–90° C./0.5 mm Hg. TLC (Silica gel: $CHCl_3$) Rf=0.38.

Sixth, 3-fluorobenzosuberone was converted into 2-amino-10-fluoro-4-oxo-5,6,7-trihydrobenzocyclohepta (6,5-d)-pyrimidine as follows. 6-ethoxycarbonyl-3-fluoro-1-benzosuberone was prepared by placing 4.77 g of 50% NaH mineral oil dispersion in a 250 ml three-necked flask, fitted with an additional funnel and a water condenser, under nitrogen atmosphere. The mineral oil was removed by washing several times with dry benzene, and the residue was then resuspended in dry benzene (60 ml). Diethylcarbonate (8.29 g) was then added in one portion. Ater refluxing, a solution of 3-fluoro-benzosuberone (6.21 g) in dry benzene (8 ml) was added dropwise to the mixture over a 3 hour period, and the refluxing was continued for another 30 minutes. The mixture was cooled to room temperature, treated with acetic acid (8.4 ml) and water (50 ml) to dissolve the solid, and the organic layer was washed several times with water and then dried over $MgSO_4$. The solvent and unreacted diethylcarbonate were removed in vacuo to give 7.92 g of product. TLC (Silica gel: $CHCl_3$) Rf=0.48.

A mixture of 6-ethoxycarbonyl-3-fluoro-1-benzosuberone (3.96 g) and guanidine carbonate (3.42 g) in ethoxyethanol (50 ml) was refluxed for 4½ hours, and, after cooling to room temperature, the solid was filtered off. After the evaporation of the solvent from the filtrate, the residue was dissolved in 2N NaOH, filtered, washed with ether, and the aqueous layer acidified to pH 5. The tan solid obtained was dissolved in hot dimethylsulfoxide (10 ml) and, while stirring, acetone (80 ml) was added. 2-amino-10-fluoro-4-oxo-5,6,7-trihydrobenzocyclohepta (6,5-d)-pyrimidine was collected as a colorless solid by filtration, washed with small amounts of acetone and ether-acetone (4:1), and then dried to yield 1.38 g. m.p. 288°–298° C. TLC (Silica gel: $CHCl_3$/MeOH=9:1) RF=0.33.

2-amino-10-nitro-4-oxo-5,6,7-trihydrobenzocyclohepta (6,5-d)-pyrimidine

To a solution of 2-amino-4-oxo-5,6,7-trihydrobenzocyclohepta (6,5-d)-pyrimidine (30 g) in concentrated sulfuric acid (150 ml) cooled to −20° C. was added dropwise fuming nitric acid (9 ml, density 1.49 g/ml). The temperature was maintained between −15° C. and −20° C. during addition. When addition was complete, the mixture was stirred at that temperature for another hour. The mixture then was poured into a large amount of ice-water (800 ml), and the solid collected by filtration and washed with cold water. The solid was dissolved in aqueous NaOH, and acetic acid was added to pH 6. The resulting solid was collected by filtration, washed with water, and dried to give 22.6 g of product. m.p. >300° C. TLC (Silica gel: $CHCl_3$/MeOH=5:1) Rf=0.51.

2,10-diamino-4-oxo-5,6,7-trihydrobenzocyclohepta (6,5-d) pyrimidine

To a solution of 2-amino-10-nitro-4-oxo-5,6,7-trihydrobenzocyclohepta (6,5-d)-pyrimidine (400 mg) in dimethylformamide (10 ml) and ethanol (2 ml) was added 10% Pd-C (100 mg). Hydrogenation was carried out under 30 psi atmosphere overnight. The mixture was then filtered through celite pad, washed with alcohol, and the solvents removed in vacuo. Following evaporation of solvent and excess HCl, the residue was recrystallized from ethanol-ether to give 200 mg of product. m.p. 200° C. (slowly decomposed. TLC (Silica gel: $CHCl_3$/MeOH=5:1) Rf=0.27.

2-amino-10-azido-4-oxo-5,6,7-trihydrobenzocyclohepta (6,5-d)-pyrimidine 5.0 g of 2-amino-10-nitro-4-oxo-5,6,7-trihydrobenzocyclohepta (6,5-d)-pyrimidine was prepared as described above and was suspended in acetic anhydride (100 ml) and refluxed for 2½ hours. It was then cooled and the colorless solid (2-acetylamino-10-nitro-4-oxo-5,6,7-trihydrobenzocyclohepta (6,5-d)-pyrimidine) was collected by filtration, washed with ether, and dried. TLC (Silica gel: $CHCl_3$/MeOH=9:1) Rf=0.61.

4.0 g of the above acetylated derivative was suspended in dimethylformamide (150 ml) and ethanol (26 ml), and 10% Pd/C (400 mg) added. Hydrogenation was carried out under 30 psi atmosphere overnight. The mixture was then filtered through celite pad, washed with ethanol, and the solvents removed in vacuo to yield 4.0 g of 2-acetyl-10-amino-4-oxo-5,6,7-trihydrobenzocyclohepta (6,5-d)-pyrimidine. TLC (Silica gel: $CHCl_3$/MeOH=9:1) Rf=0.31.

600 mg of the above acetylated 10-amino derivative was suspended in methanol (20 ml) and excess methanolic HCl added. A clear solution initially formed which subsequently became a suspension. The solvent and excess HCl were then removed in vacuo at room temperature to dryness. Next, the solid was resuspended in cold water (20 ml), treated with 2N HCl (1.5 ml) and a cold solution of sodium nitrite (300 mg) in water (2 ml), and then stirred at 0°–5° C. for 15 min. A yellow suspension formed, to which was then added a cold solution of sodium azide (300 mg) in water (2 ml). The mixture was stirred for 20 min. at 0°–5° C., after which the colorless solid (2-acetylamino-10-azido-4-oxo-5,6,7-trihydrocyclohepta (6,5-d)-pyrimidine) was collected by filtration, washed with cold water, and dried. TLC (Silica gel: $CHCL_3$/MeOH=9:1) Rf=0.71.

The above acetylated derivative was deacetylated to form 2-amino-10-azido-4-oxo-5,6,7-trihydrocyclohepta (6,5-d)-pyrimidine by suspending the derivative (560 mg) in methanol (20 ml) and adding methanolic HCl (2 ml). The mixture was refluxed for 2 hours, and then cooled. The resulting pale grey solid was filtered off, concentrated in vacuo to dryness, and then triturated with ethyl acetate to yield 280 mg of the deacetylated product. m.p. 178° C. (slowly decomposed). TLC (Silica gel: $CHCl_3$/MeOH=9:1) Rf=0.35. IR (Nujol) 2120 $cm^{-1}$ (azide).

When administered to mammals (e.g., orally, nasally, topically, parenterally, intravenously, or by suppository), the compounds have an antiviral effect, and are particularly effective against herpes simplex viruses occurring in the eye, cutaneously, orally, genitally, or in upper respiratory areas.

Good in vivo test results, compared to in vitro results, suggest that the compounds, rather than acting directly on the virus, act via immunomodulation (e.g., delayed-type-hypersensitivity stimulation). The compounds should therefore also be useful in treating other types of infections (e.g., bacterial or fungal), tumors, and arthritis. The compounds have been found to be effective anticancer agents, particularly against melanoma, when administered alone or, more preferably, in combination with other anticancer agents, e.g., cytoxin or DTIC.

The compounds can be administered to a mammal, e.g. a human, in a dosage of 25 to 300 mg/kg/day, preferably 100 to 200 mg/kg/day.

Referring again to the FIGURE, when it is desired to apply the compound topically, sealed envelope 12 containing the impregnated towlette 10 is torn open and the towlette is removed and used, and the packet and used towlette are then discarded.

The impregnated towlette can be used in the treatment and/or prevention of herpes simplex type II infections. In the case of the treatment of a skin lesion associated with herpes, the impregnated towlette can be used to apply the compound to the affected area and then discarded. For prevention of herpes infections, the impregnated towlette can be used to apply the compound to an area which the user suspects has been recently exposed to herpes virus, e.g., to the genitals following sexual relations.

Other Embodiments

Other embodiments are within the following claims. For example, the impregnated sheet can be, in addition to absorbant paper, another suitable material such as unwoven fabric. Instead of sealing wet towlettes in individual packets, multiple impregnated sheets can be provided in one container, e.g., a jar or a metal or plastic can. Impregnated towlettes can be used to treat or prevent other viral or bacterial infections, e.g., the common cold; for treatment of colds, for example, facial tissues can be impregnated with the compounds, application of the tissue to the nose providing the compound to that area.

I claim:

1. A compound having the formula:

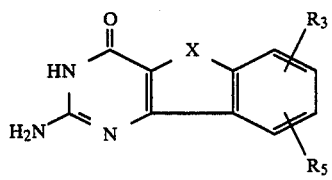

wherein
X is $(CH_2)_n$ where $1 \leq n \leq 3$, or

where $R^4$ is lower alkyl; and $R^3$ and $R^5$, independently, are H, fluoro, nitro, amino, lower alkylamino, lower dialkylamino; arylamino (wherein aryl does not include aromatic heterocycle), acylamido, carboxy, azido, lower alkoxy, trimethylsulfonyl, trifluoromethanesulfonyl, or lower alkoxycarbonyl, provided that when X is $(CH_2)_2$, $R^3$ cannot be H or lower alkoxy; or a pharmaceutically acceptable salt thereof.

2. A compound having the formula

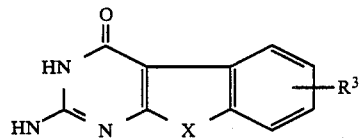

wherein
X is $(CH_2)_n$ where $1 \leq n \leq 3$, or

where $R^4$ is lower alkyl; and
$R^3$ is fluoro, nitro, amino, lower alkylamino; lower dialkylamino, arylamino (wherein aryl does not include aromatic heterocycle), acylamido, carboxy, or lower alkoxycarbonyl; or a pharmaceutically acceptable salt thereof.

3. The compound of claim 1, wherein X is $(CH_2)_3$, $R^3$ is fluoro, and $R^5$ is H
said compound having the formula 2-amino-10-fluoro-4-oxo-5,6,7-trihydrobenzocyclohepta (6,5-d)-pyrimidine.

4. The compound of claim 1, wherein X is $(CH_2)_3$, $R^3$ is nitro, and $R^5$ is H
said compound having the formula 2-amino-10-nitro-4-oxo-5,6,7-trihydrobenzocyclohepta (6,5-d)-pyrimidine.

5. The compound of claim 1, wherein X is $(CH_2)_3$, $R^3$ is amino, and $R^5$ is H
said compound having the formula 2,10-diamino-4-oxo-5,6,7-trihydrobenzocyclohepta (6,5-d)-pyrimidine.

6. The compound of claim 1, wherein X is $(CH_2)_3$, $R^3$ is azido, and $R^5$ is H
said compound having the formula 2-amino-10-azido-4-oxo-5,6,7-trihydrobenzocyclohepta (6,5-d)-pyrimidine.

7. A biological response modifying composition comprising an effective amount of the compound of claim 1, or 2, together with a pharmaceutically acceptable carrier substance.

8. The composition of claim 7 wherein said composition is in the form of a pill, capsule, or tablet for oral administration to a human patient in need of said compound.

9. The composition of claim 7 wherein said composition is in the form of an ointment, lotion, cream, powder, gel, or spray for application to the skin of a human patient in need of said compound.

10. An anti-herpes simplex type II compound as set forth in any one of claims 1, or 2.

* * * * *

UNITED STATES PATENT AND TRADEMARK OFFICE
CERTIFICATE OF CORRECTION

PATENT NO. : 4,814,335
DATED : March 21, 1989
INVENTOR(S) : Sun H. Kim

It is certified that error appears in the above-identified patent and that said Letters Patent is hereby corrected as shown below:

Column 2, lines 15-20, change the chemical structure to read as highlighted in red as follows:

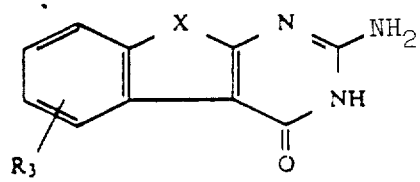

Column 2, line 22, change "of" to --or--;

UNITED STATES PATENT AND TRADEMARK OFFICE
CERTIFICATE OF CORRECTION

PATENT NO. : 4,814,335

DATED : March 21, 1989

INVENTOR(S) : Sun H. Kim

It is certified that error appears in the above-identified patent and that said Letters Patent is hereby corrected as shown below:

Column 8, lines 10-15, change the chemical structure to read as highlighted in red as follows:

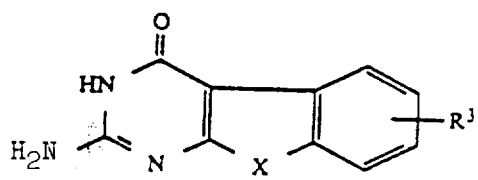

Signed and Sealed this

Twenty-seventh Day of March, 1990

Attest:

JEFFREY M. SAMUELS

Attesting Officer

Acting Commissioner of Patents and Trademarks